(12) United States Patent
Letort (10) Patent No.: US 7,044,920 B2
(45) Date of Patent: May 16, 2006

(54) PRESSURE MONITORING SYSTEM TO PREVENT ANEURISMAL SAC RUPTURE

(75) Inventor: Michel Letort, Prevessins (FR)

(73) Assignee: Medtronic Vascular, Inc., Santa Rosa, CA (US)

( * ) Notice: Subject to any disclaimer, the term of this patent is extended or adjusted under 35 U.S.C. 154(b) by 391 days.

(21) Appl. No.: 10/422,358

(22) Filed: Apr. 24, 2003

(65) Prior Publication Data

US 2004/0215100 A1   Oct. 28, 2004

(51) Int. Cl.
*A61B 5/00* (2006.01)
(52) U.S. Cl. .................................... 600/561
(58) Field of Classification Search ............... 600/488, 600/486, 500, 505, 302, 561; 709/223, 224; 128/899
See application file for complete search history.

(56) References Cited

U.S. PATENT DOCUMENTS

| | | | |
|---|---|---|---|
| 6,159,156 A | 12/2000 | Van Bockel | |
| 6,682,490 B1 * | 1/2004 | Roy et al. | 600/486 |
| 2002/0183629 A1 * | 12/2002 | Fitz | 600/488 |
| 2003/0041135 A1 * | 2/2003 | Keyes et al. | 709/223 |

* cited by examiner

*Primary Examiner*—Max F. Hindenburg
*Assistant Examiner*—Brian Szmal (57) ABSTRACT

An abdominal aortic aneurysm pressure monitoring system comprising at least one pressure sensor positioned in an aneurismal sac which optionally may be excluded from direct arterial pressure by an already implanted stent graft, at least one pressure sensor positioned in an abdominal region of the body at a location outside of the aneurismal sac, a controller in communication with the pressure sensors, where a pressure gradient between the abdominal region and the aneurismal sac is determined based on the pressures communicated to the controller from the aneurismal sac and abdominal region pressure sensors.

22 Claims, 8 Drawing Sheets

FIG. 8

PRESSURE MONITORING SYSTEM TO PREVENT ANEURISMAL SAC RUPTURE

FIELD OF THE INVENTION

This invention relates generally to a pressure monitoring system. More specifically the invention relates to monitoring pressure gradient between an aneurismal sac and the abdominal cavity to prevent rupture of the aneurismal sac.

BACKGROUND OF THE INVENTION

Vascular aneurysms are produced when a thinning or weak spot in a vessel wall dilates eventually posing a health risk from its potential to rupture, clot, or dissect. While aneurysms can occur in any blood vessel, most occur in the aorta and peripheral arteries. The majority of aortic aneurysms occur in the abdominal aorta, usually beginning below the renal arteries and often extending into one or both of the iliac arteries. The etiology of aneurysm formation is not entirely understood, but is thought to be related to congenital thinning of the artery, atherosclerotic vessel degeneration, vessel trauma, infection, smoking, high blood pressure, and other causes leading to vessel degeneration. Left untreated, aneurysms may lead to gradual vessel expansion, thrombus formation leading to stroke or other vessel blockage, vessel rupture, shock, and eventual death.

After a successful endovascular aneurysm repair with an absence of endovascular leakage, prior art techniques use the intra-aneurysm pressure to control the exclusion of the aneurismal sac from the main blood circulation by providing hemodynamic information within the sac to determine if an additional procedure is warranted. Pressure sensors to monitor the aneurismal sac are conventionally done by monitoring a pressure gradient between the artery, such as the aorta and the aneurismal sac. But the risk of rupture is not most accurately measured from this pressure gradient, but rather from the pressure gradient between the aneurismal sac and the abdominal cavity.

Therefore, it would be desirable to provide an aneurysm pressure monitoring system, which monitors the pressure gradient most likely to predict a rupture.

SUMMARY OF THE INVENTION

One aspect according to the present invention provides first an abdominal aortic aneurysm pressure monitoring system comprising at least one pressure sensor positioned in an aneurismal sac of a body and at least one pressure sensor positioned in an abdominal region of the body outside of the aneurismal sac, where a controller is in communication with the pressure sensors. A pressure gradient between the abdominal region and the aneurismal sac is determined based on the pressures communicated to the controller from the aneurismal sac and abdominal region pressure sensors.

Another aspect according to the present invention is a method for monitoring an abdominal aortic aneurysm, including sensing pressure in an aneurismal sac of a body, sensing pressure in an abdominal region of the body, (preferably retroperitoneal), the abdominal region being outside of the aneurismal sac, determining a pressure gradient based on the sensed abdominal region pressure and the sensed aneurismal sac pressure.

Another aspect according to the present invention is a system for monitoring an abdominal aortic aneurysm, which comprises a means for sensing pressure in an aneurismal sac of a body, a means for sensing pressure in an abdominal region of the body located outside of the aneurismal sac, a means for determining a pressure gradient based on the sensed abdominal region pressure and the sensed aneurismal sac pressure.

An additional aspect according to the present invention is a computer readable medium storing a computer program comprising computer readable code for receiving a cavity pressure from a cavity sensor positioned in an aneurismal cavity of a body, computer readable code for receiving an abdomen pressure from an abdominal sensor positioned in an abdominal region of the body outside of the aneurismal cavity, and computer readable code for calculating a pressure gradient based on the received sac pressure and abdomen pressure.

The forgoing device and other devices as well as features and advantages of the present invention will become further apparent from the following detailed description of the presently identified embodiments, read in conjunction with the accompanying drawings. The detailed description and drawings are merely illustrative of the present invention rather than limiting, the scope of the present invention being defined by the appended claims and equivalents thereof.

BRIEF DESCRIPTION OF THE DRAWINGS

Embodiments according to the present invention are illustrated by way of example and not limitation in the accompanying figures, in which like references indicate similar elements, and in which.

DETAILED DESCRIPTION

Figure 1:
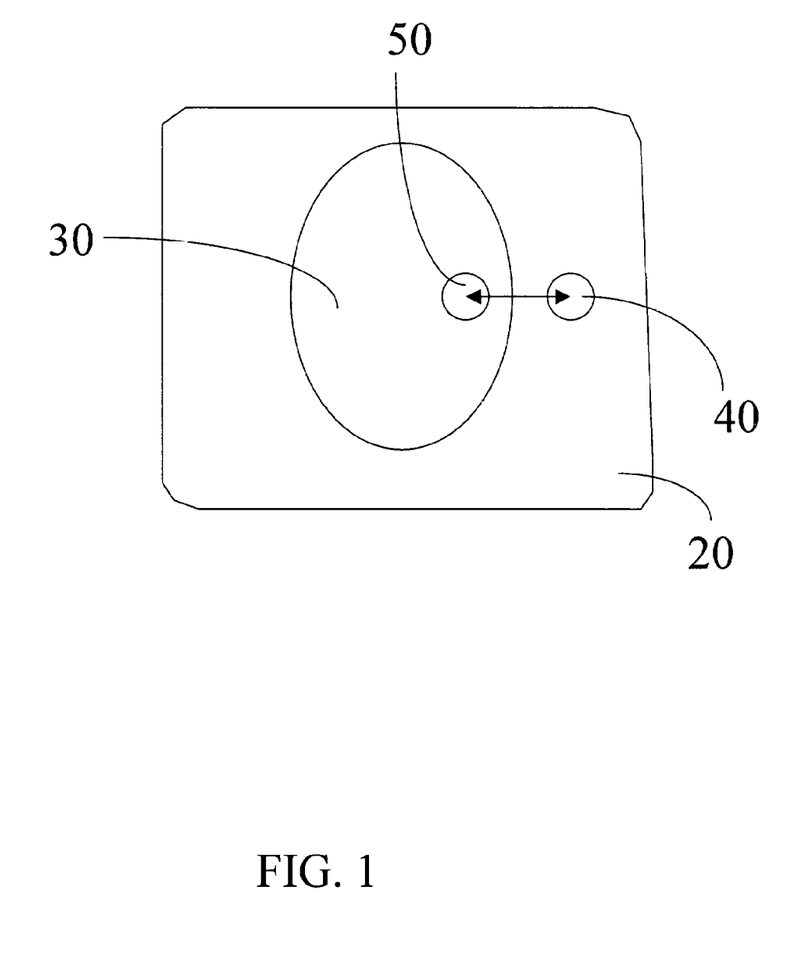
FIG. 1 illustrates a schematic diagram of a first embodiment of sensor locations for monitoring the pressure of an abdominal aortic aneurysm.

FIG. 1 illustrates schematically an abdominal cavity 20 in relation to an aneurismal sac 30 with a sac sensor 50 positioned in (or on) the aneurismal sac 30, usually in a sac excluded by a stent graft, where hereinafter reference to a sac will be understood to include the aneurismal sac excluded by a stent graft. FIG. 1 also illustrates an abdominal sensor 40 located in the abdominal cavity 20, where the sac sensor 50 and the abdominal sensor 40 are part of a system to monitor the pressure of the abdominal aortic aneurysm. Preferably the abdominal sensor 40 is located at the level of the retro peritoneum. The sac sensor 50 and the abdominal sensor 40 are positioned to provide data to determine a pressure gradient, illustrated as a double arrow between the sac sensor 50 and the abdominal sensor 40, between the aneurismal sac 30 and the abdominal cavity 20. It is this pressure gradient that is most relevant in the determination of the likelihood of an aneurismal sac 30 rupture.

Figure 2:
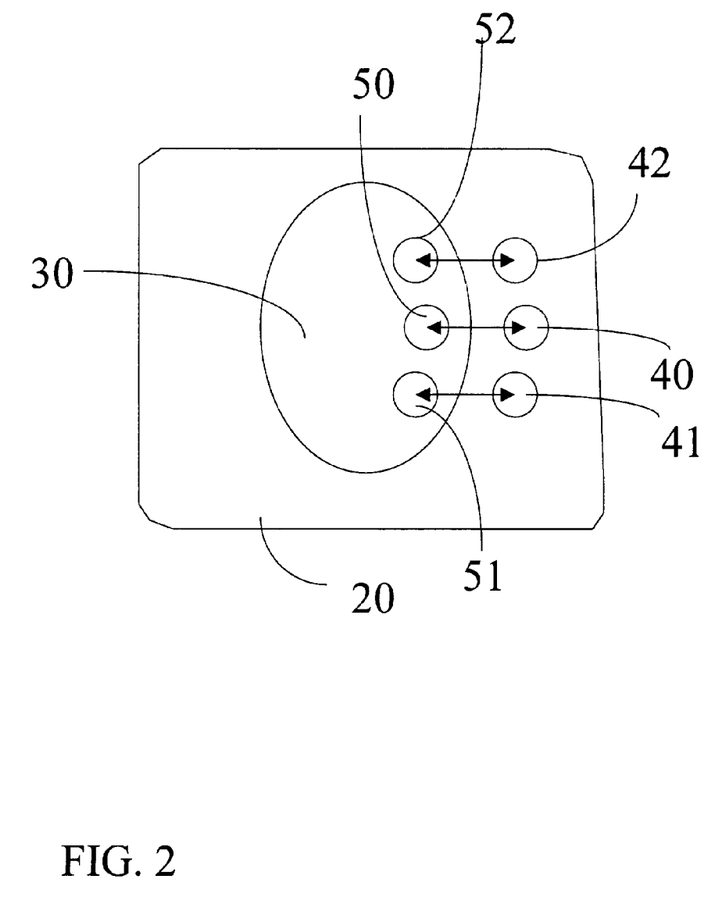
FIG. 2 illustrates a schematic diagram of a second embodiment of sensor locations for monitoring the pressure of an abdominal aortic aneurysm.

FIG. 2 illustrates schematically a plurality of abdominal sensors 40, 41, 42 in relation to a plurality of sac sensors 50, 51, 52. The abdominal sensors 40, 41, 42 are located in multiple positions in the abdominal cavity 20 and the sac sensors 50, 51, 52 are located on the aneurismal sac 30. A plurality of abdominal sensors 40, 41, 42 and sac sensors 50, 51, 52 provides a more accurate measurement of the pressure gradient and improves the probability of accurately predicting an aneurismal sac 30 rupture.

The abdominal sensors 40, 41, 42 and sac sensors 50, 51, 52 can be placed in position within the abdominal cavity 20 and the aneurismal sac 30 using a catheter. Insertion of such sensors and similar small devices in a body is a technique, which is frequently used in the medical profession and is known to those of ordinary skill in the art.

Figure 3:
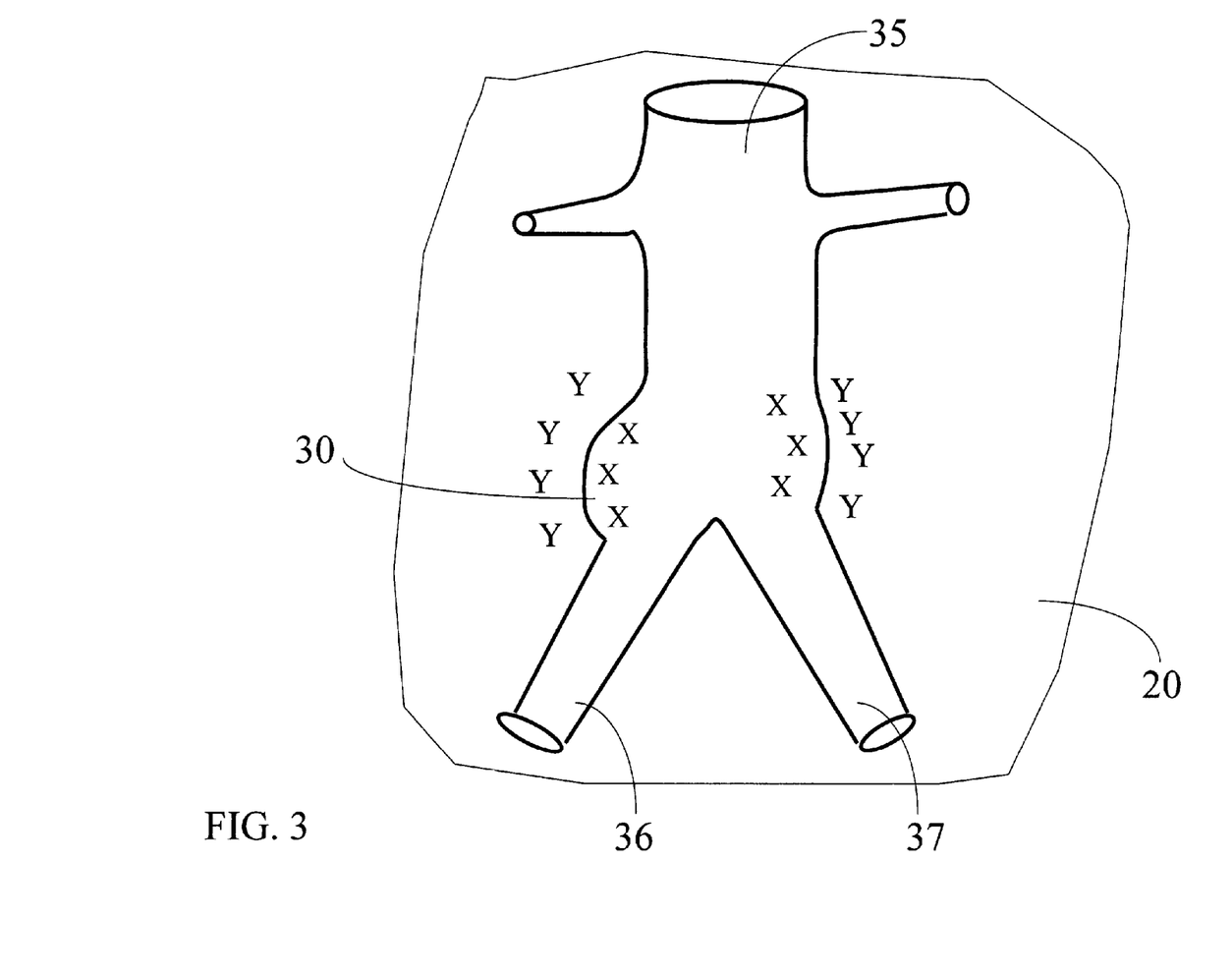
FIG. 3 illustrates a schematic diagram of several options for sensor locations for monitoring the pressure of an abdominal aortic aneurysm.

FIG. 3 illustrates an aneurismal sac 30 in relation to the abdominal aorta 35, first iliac artery 36 and second iliac artery 37 and the abdominal cavity 20. The X's marked on the aneurismal sac 30 indicate possible areas to place sac sensors 50, 51, 52 as part of the system to measure the pressure gradient. The Y's marked on the abdominal cavity 20 indicate possible areas to place the abdominal sensors 40, 41, 42 in the retro peritoneum. One or more pressure sensors can be placed on one or more of the X's and Y's.

Figure 4:
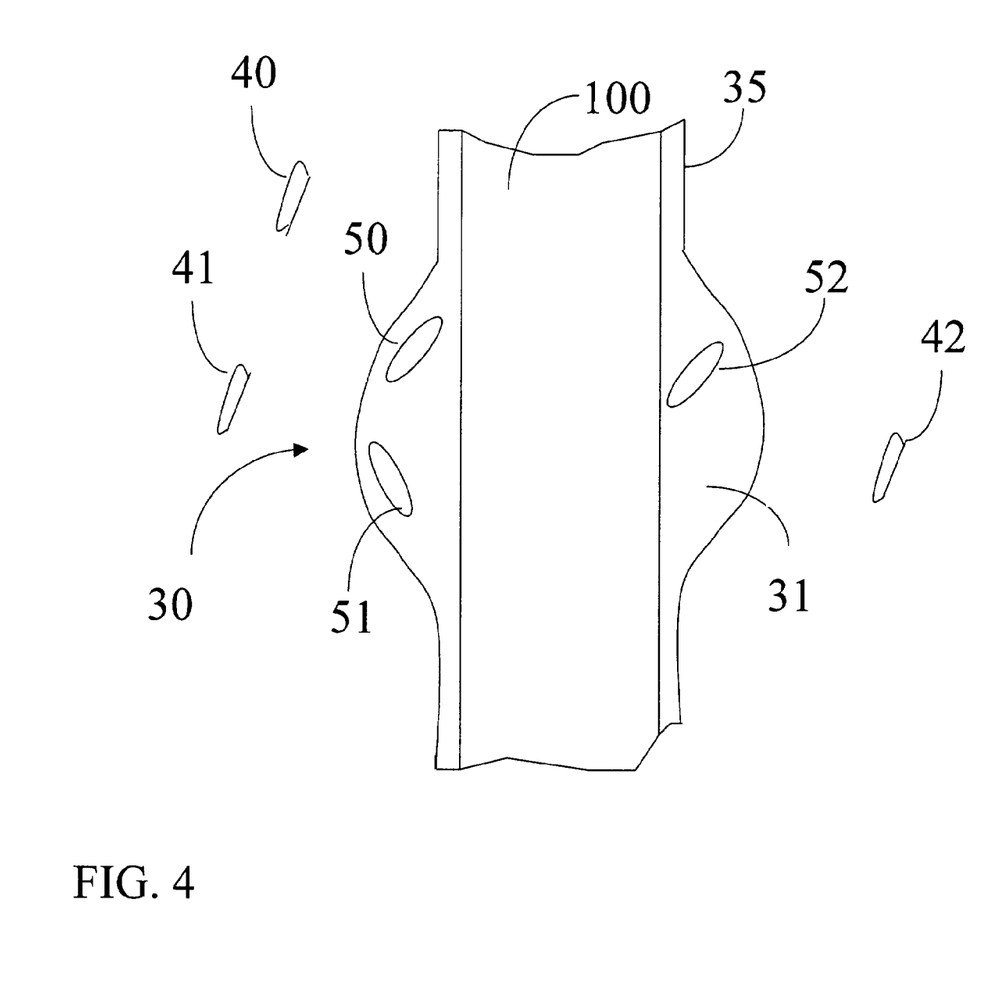
FIG. 4 illustrates a schematic diagram of a third embodiment of sensor locations form monitoring the pressure of an abdominal aortic aneurysm with an implanted stent graft.

FIG. 4 illustrates an aneurismal sac 30 which may be excluded from direct arterial pressure by an implanted stent or a stent graft 100, which is inserted into the aorta 35 by a catheter. The sac sensors 50, 51, 52 are held within in the sac region 31 between the stent graft 100 and the wall of the aneurismal sac 30 in order to measure the pressure gradient with respect to the abdominal sensors 40, 41, 42.

Figure 5:
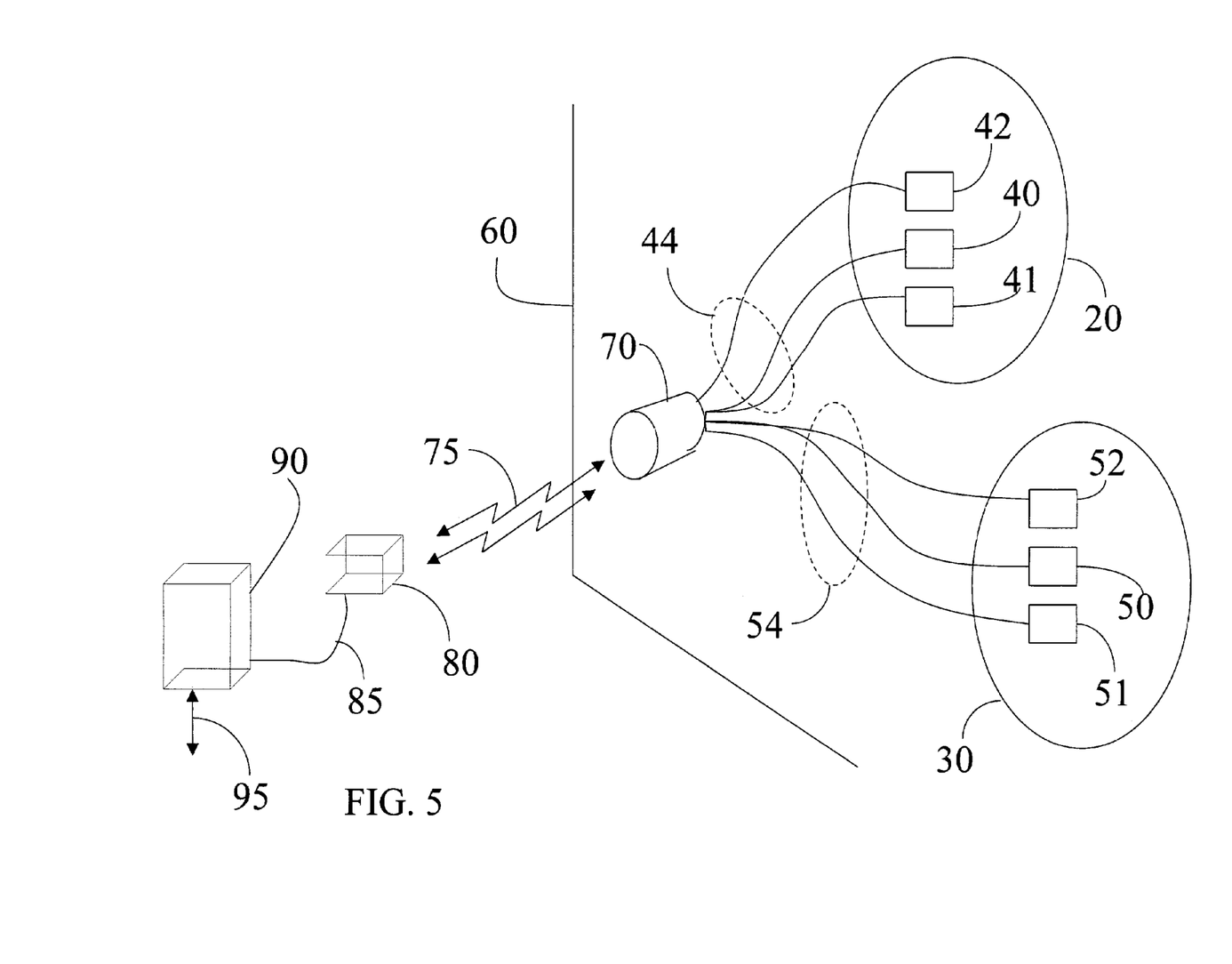
FIG. 5 illustrates a schematic diagram of a first embodiment of a system to monitor the pressure of abdominal aortic aneurysm according to the present invention.

FIG. 5 schematically illustrates an embodiment of a system to monitor the pressure of abdominal aortic aneurysm. The aneurismal sac 30 has three sac sensors 50, 51, 52 attached to it and there are three abdominal sensors 40, 41, 42 in the abdominal cavity 20. The sac sensors 50, 51, 52 are connected by leads 54 to controller 70 and abdominal sensors 40, 41, 42 are connected by leads 54 to the same controller 70. Controller 70 is implanted inside the body surface 60. Controller 70 receives the pressure input from the sac sensors 50, 51, 52 and abdominal sensors 40, 41, 42 and then transmits that data by a radio frequency signal 75 to a radio frequency interface 80. The radio frequency interface 80 is in electrical communication by wire 85 with computer 90, or any programmable system for data acquisition and analysis. In another embodiment of a network configuration the computer 90 can receive the wireless communication, using a WiFi type of interface in the computer 90, with no radio frequency interface 80 in electrical communication by wire 85 with computer 90.

Computer 90 contains software to perform calculations on the received pressure data to determine the pressure gradient between the sac sensors 50, 51, 52 and abdominal sensors 40, 41, 42. Computer 90 also contains software to store data over time and to compare the pressure gradient to a pressure gradient limit. The pressure data can be tracked and plotted over a period of time to provide data on any trends or variations in the pressure within the aneurismal sac 30. Additionally, each of the sac sensors 50, 51, 52 and abdominal sensors 40, 41, 42 may have an IP address, or any other type of network address, to provide the capability to individually interrogate any sensor on the sensor network. In this manner, sensors in more critical areas can be interrogated much more frequently than others. A TCP/IP protocol may be used, but there are other possibilities, such as, for example, simple packet protocols. More sophisticated devices may be used, where each of sac sensors 50, 51, 52 and abdominal sensors 40, 41, 42 can be a transponder for another nearby sensor in a star or ring network configuration. The computer 90 may be programmed to control interrogations of the sac sensors 50, 51, 52 and abdominal sensors 40, 41, 42 and the interactions of a network of sac sensors 50, 51, 52 and abdominal sensors 40, 41, 42.

Computer 90 is connected to a computer network (not shown), preferably the Internet, via the network connection 95. Transmitted data, which and includes pressure measurements and any relevant calculations on the data, is sent to a physician or other appropriate personnel for review. The computer can compare a target pressure gradient with the measured pressure gradient and send warnings to a physician or other appropriate personnel when the pressure gradient exceeds the target pressure gradient. Additionally, any other equivalent and relevant physiologic profile indicative of a problem based on the measured pressures can be used to trigger a warning when the profile meets or exceeds a pre-set limit, pre-established parameters or an established algorithm. The physician or other appropriate personnel can be warned by, for example, a page sent to the appropriate person's pager or by an audible warning tone on the appropriate person's computer. This allows the physician to take appropriate steps for the patient, perhaps, by performing an emergency surgery, in order to prevent an impending rupture from occurring. If the physician is notified of a trend that needs to be monitored more closely, instructions can be sent via the network connection 95 to the computer 90 requesting to interrogate the sensors in the required manner. The computer 90 will send required code to the radio frequency interface 80 to trigger the controller 70 as needed. The sac sensors 50, 51, 52 and abdominal sensors 40, 41, 42 can be addressed using the IP address of the sac sensors 50, 51, 52 and abdominal sensors 40, 41, 42.

Figure 6:
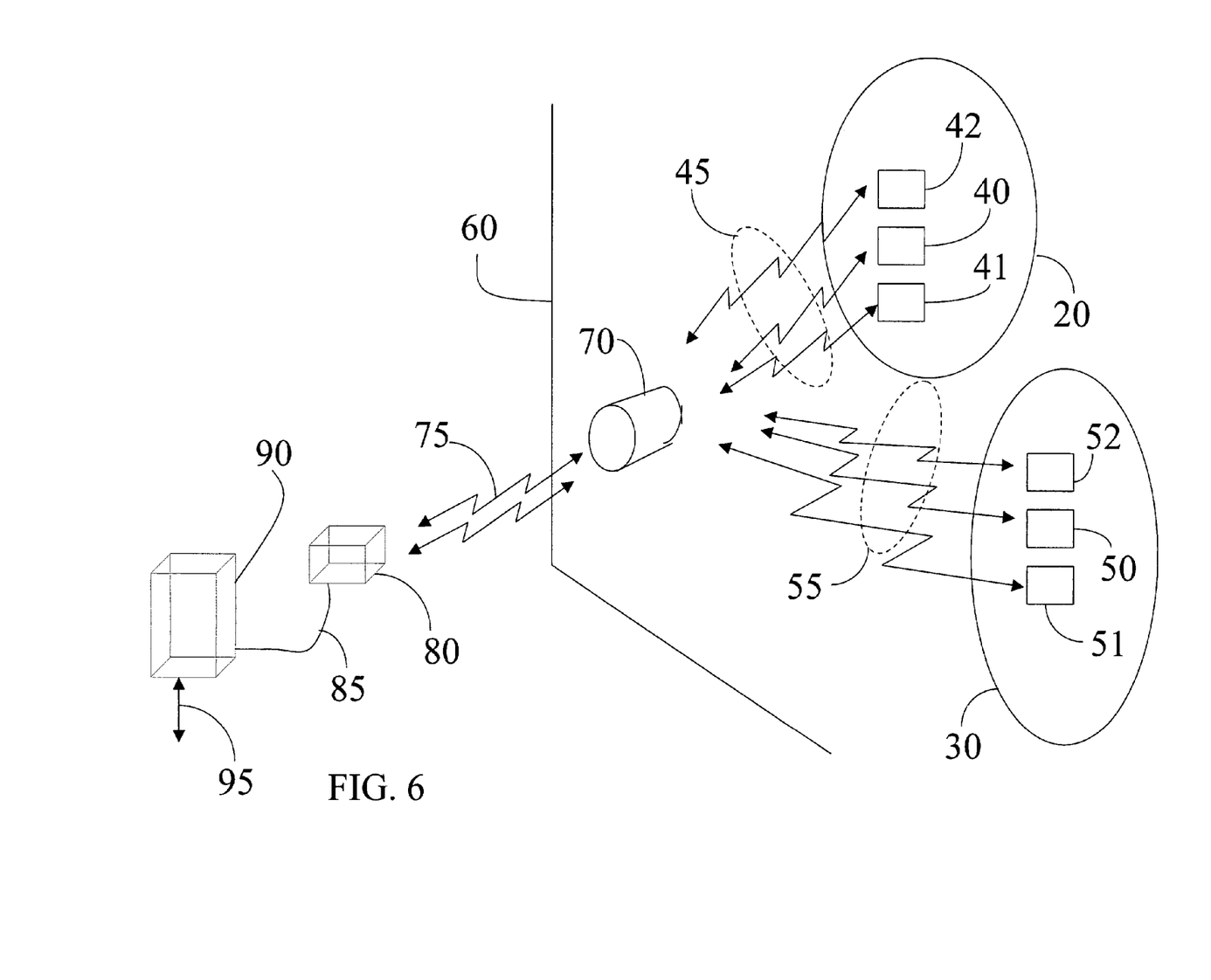
FIG. 6 illustrates a schematic diagram of a second embodiment of a system to monitor the pressure of abdominal aortic aneurysm according to the present invention.

FIG. 6 illustrates another embodiment of a system to monitor the pressure of abdominal aortic aneurysm. In this system the electrical leads 44 and 54 are replaced by a wireless communication between the sac sensors 50, 51, 52 and the controller 70, as well as, between the abdominal sensors 40, 41, 42 and the controller 70. The radio frequency emission 45 and 55, represented by jagged double-arrowhead lines, indicate this radio frequency communication. As in FIG. 5, the controller 70 is implanted inside the body surface 60. Controller 70 receives the pressure input from the sac sensors 50, 51, 52 and abdominal sensors 40, 41, 42 and then transmits that data by a radio frequency signal 75 to a radio frequency interface 80. The radio frequency interface 80 is in electrical communication by wire 85 with computer 90, which is connected to a computer network or the Internet by the network connection 95. The network connection 95 can be wired or wireless.

Figure 7:
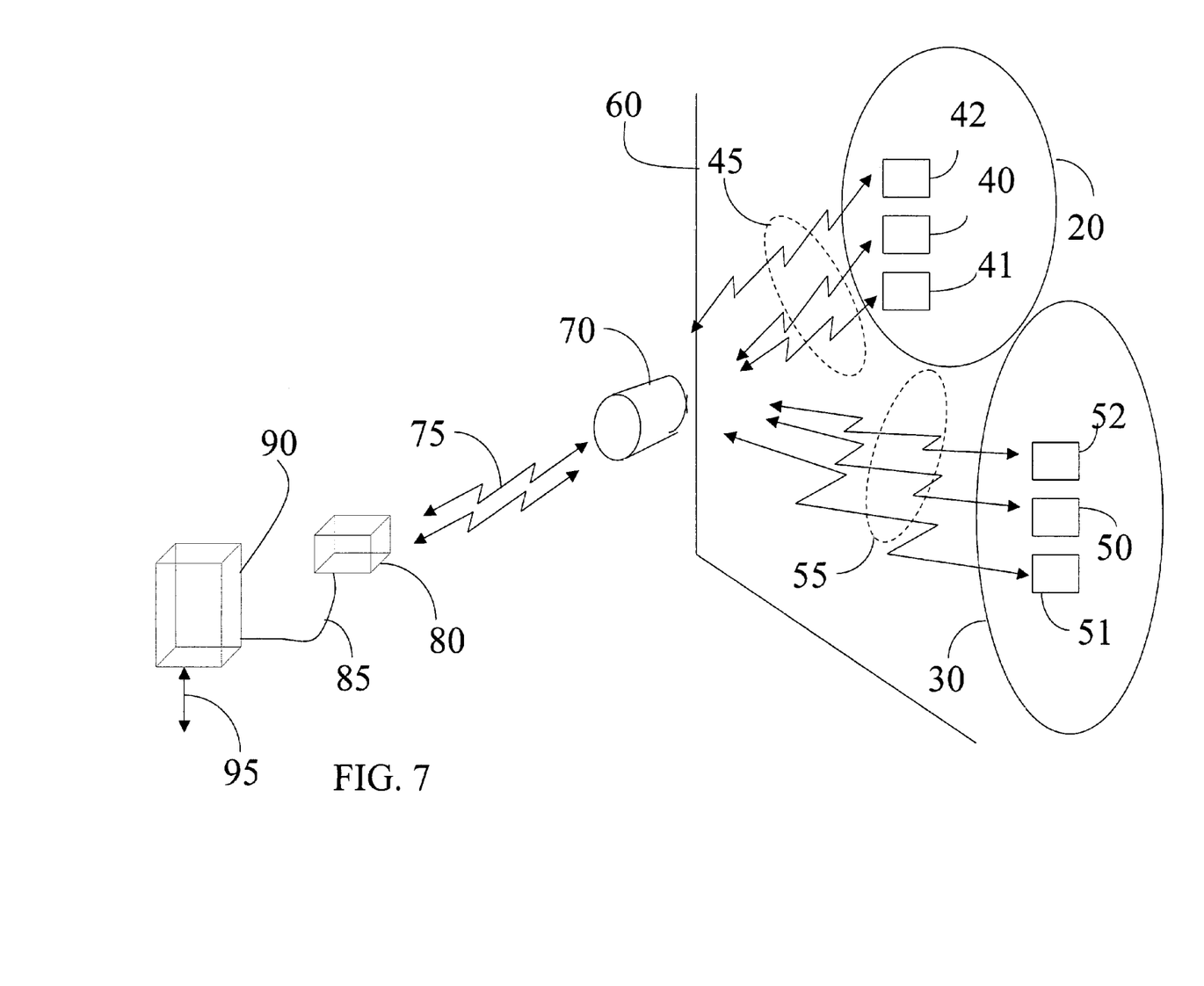
FIG. 7 illustrates a schematic diagram of a third embodiment of a system to monitor the pressure of abdominal aortic aneurysm according to the present invention.

FIG. 7 illustrates an additional embodiment of a system to monitor the pressure of abdominal aortic aneurysm. In this system there is wireless data communication between the sac sensors 50, 51, 52 and the controller 70, as well as, between the abdominal sensors 40, 41, 42 and the controller 70. The jagged radio frequency emission lines 45 and 55 indicate this data transfer. In this embodiment the controller 70 is outside the body surface 60. It can be attached by some means, such as, for example tape or a bandage, or held outside but close to the body like a pager to the body surface 60. Alternately, the controller 70 can be a device to periodically bring into contact with the body surface 60. If the power level of the controller 70 is adequate, then the patient may only need to be in the room with the controller 70 for the data signals to be transmitted. The typical wireless system operates using inductance between inductors on the controller 70 and the sac sensors 50, 51, 52 and between the controller 70 and abdominal sensors 40, 41, 42, as is known to those of ordinary skill in the art. The controller 70 receives the pressure input from the sac sensors 50, 51, 52 and abdominal sensors 40, 41, 42 and then transmits that data by a radio frequency signal 75 to a radio frequency interface 80. The radio frequency interface 80 is in electrical communication by wire 85 with computer 90, which is connected to a computer network or the Internet by the network connection 95. The network connection 95 can be wired or wireless. If the computer 90 has a WiFi interface then the radio frequency interface 80 in electrical communication by wire 85 is not needed. The controller 70 can input data directly to the computer 90.

Figure 8:
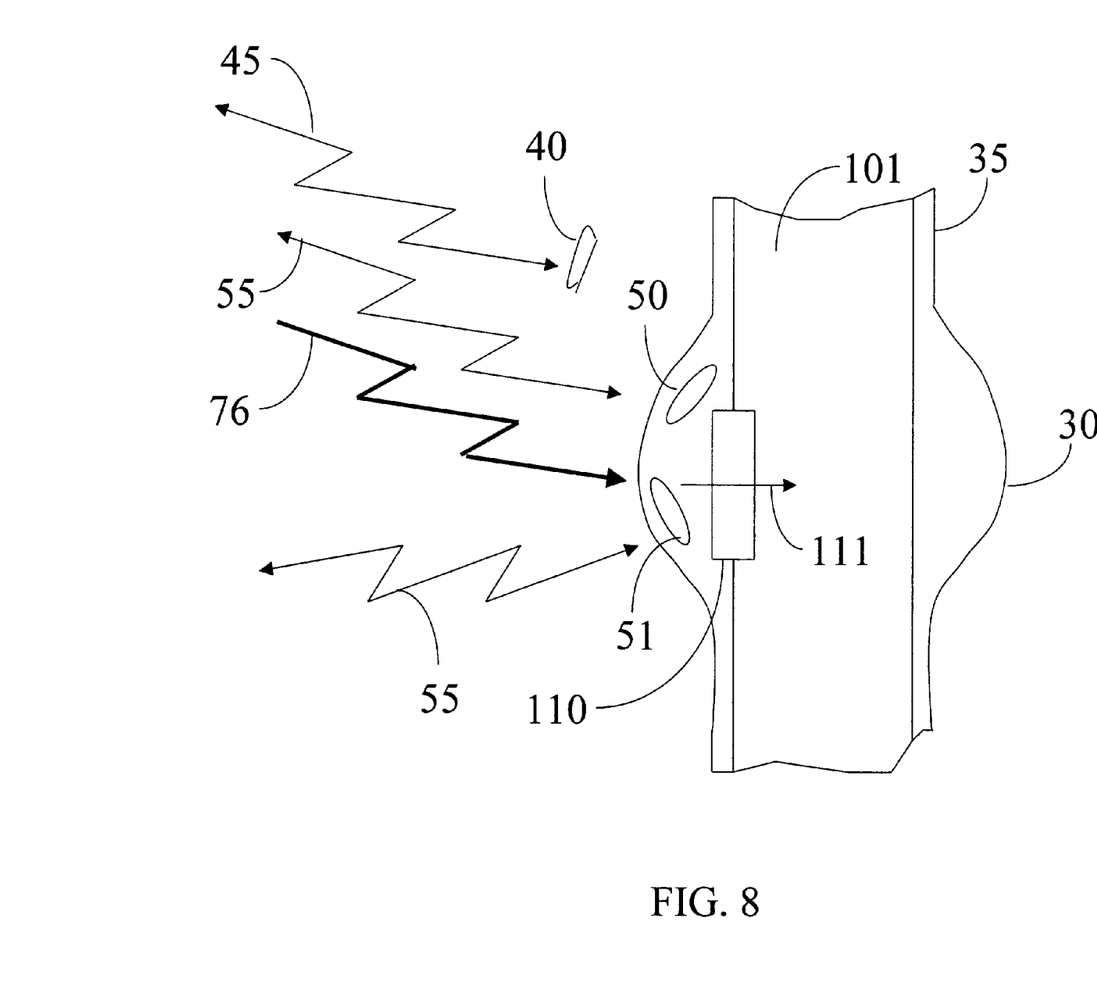
FIG. 8 illustrates a schematic diagram of an implementation of a micro-pump in the system to monitor the pressure of abdominal aortic aneurysm.

FIG. 8 illustrates sac sensors 50 and 51 in the aneurismal sac 30. A stent or stent graft 101, which has a micro-pump 110 embedded in its wall, is inserted into the aorta 35, illustrated in FIG. 3, by a catheter. When the pressure data transmitted on the radio frequency emission 55 indicates a dangerous pressure level relative to the pressure data from abdominal sensor 40 in the abdominal cavity (not labeled) transmitted on the radio frequency emission 45, the computer 90 (not shown) be programmed to react. The computer 90 (not shown) can direct a the micro-pump 110 on radio frequency emission 76 to pump material, as shown by the straight arrow 111, from the portion of the aneurismal sac 30 outside the stent 100 into the stent 100 to reduce the pressure inside the aneurismal sac 30. Micro-pumps can be made using micro-electro-machining system (MEMS) technology and are operable by several methods including, but not limited to, piezo, electrostatic, electromagnetic or pneumatic. Techniques to fabricate and operate micropumps are known to those of ordinary skill in the art. For this technology the piezo or electromagnetic are preferred.

Clearly, the illustrated embodiments of an abdominal aortic aneurysm pressure monitoring system are meant to illustrate what system can be configured to measure the pressure gradient between an aneurismal sac 30 and an abdominal cavity 20 and to store the pressure data and/or respond with a warning or an action such as pumping, and is not intended to be exhaustive of all possibilities or to limit what can be configured for the aforementioned purpose. There is therefore a multiplicity of other possible combinations and embodiments. By using what is shown and described herein, the pressure monitoring of an aneurismal sac is more accurate. Those having ordinary skill in the art will therefore appreciate the benefit of employing an abdominal aortic aneurysm pressure monitoring system in numerous and various system designs.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. An abdominal aortic aneurysm pressure monitoring system for an aortic aneurysm in an arterial system, comprising:
   at least one pressure sensor positioned in an aneurismal sac of a body;
   at least one pressure sensor positioned in an abdominal region of the body at a location outside of the aneurismal sac; and
   a controller in communication with the pressure sensors, wherein a pressure gradient outside the arterial system between the abdominal region and the aneurismal sac is determined based on the pressures communicated to the controller from the aneurismal sac and abdominal region pressure sensors.

2. The system of claim 1, wherein the controller is positioned within a body.

3. The system of claim 1, wherein the controller is in wireless communication with the sensors.

4. The system of claim 1, wherein each sensor has an assigned IP address.

5. The system of claim 1, wherein the controller communicates with a computer or a computer network.

6. The system of claim 1, wherein the controller communicates with a computer or a computer network via a radio frequency interface.

7. The system of claim 5, wherein pressure data communicated from the controller to the computer network is stored in the computer network.

8. The system of claim 5, wherein a warning signal is sent in response to a pressure gradient target being met from the controller or computer in communication with the controller.

9. The system of claim 1, wherein the abdominal sensor is positioned at a level of the retro peritoneum.

10. The system of claim 1, further comprising:
    a micropump positioned to relieve pressure to the aneurismal sac in response to a pressure gradient target being exceeded.

11. The system of claim 1, wherein the pressure gradient is determined at the controller or computer.

12. The system of claim 1, further comprising:
    a stent graft implanted in the aneurismal sac of a body, wherein the at least one pressure sensor positioned in the aneurismal sac of the body is located outside the stent graft.

13. A method for monitoring an abdominal aortic aneurysm in an arterial system, the method comprising:
    sensing pressure in an aneurismal sac of a body;
    sensing pressure in an abdominal region of the body, the abdominal region being outside of the aneurismal sac; and
    determining a pressure gradient outside the arterial system based on the sensed abdominal region pressure and the sensed aneurismal sac pressure.

14. The method of claim 13, further comprising:
sending the sensed abdominal region and aneurismal sac pressures over a wireless network.

15. The method of claim 13, further comprising:
storing the determined gradient in a memory in communication with the wireless network.

16. The method of claim 13, further comprising:
sending a warning signal when the determined gradient meets a pre-set limit.

17. A system for monitoring an abdominal aortic aneurysm in an arterial system, comprising:
means for sensing pressure in an aneurismal sac of a body;
means for sensing pressure in an abdominal region of the body located outside of the aneurismal sac; and
means for determining a pressure gradient outside the arterial system based on the sensed abdominal region pressure and the sensed aneurismal sac pressure.

18. The system of claim 17, further comprising:
means for sending the sensed abdominal and sac pressures over a wireless network.

19. The system of claim 17, further comprising:
means for sending a warning when the determined gradient meets a pre-set limit.

20. A computer readable medium storing a computer program comprising:
computer readable code for receiving a sac pressure from a sac sensor positioned in an aneurismal sac of a body;
computer readable code for receiving an abdomen pressure from an abdominal sensor positioned in an abdominal region of the body outside of the aneurismal sac; and
computer readable code for calculating a pressure gradient outside an arterial system based on the received sac pressure and abdomen pressure.

21. The medium of claim 20, further comprising
computer readable code for comparing the calculated pressure gradient with pre-established parameters; and
computer readable code for warning appropriate personnel if the pressure gradient exceeds the pre-established parameters.

22. An abdominal aortic aneurysm pressure monitoring system, comprising:
at least one pressure sensor positioned in an aneurismal sac of a body;
at least one pressure sensor positioned in an abdominal region of the body at a location outside of the aneurismal sac;
a controller in communication with the pressure sensors, wherein a pressure gradient between the abdominal region and the aneurismal sac is determined based on the pressures communicated to the controller from the aneurismal sac and abdominal region pressure sensors; and
a micropump positioned to relieve pressure to the aneurismal sac in response to a pressure gradient target being exceeded.

* * * * *